United States Patent
Ford et al.

(10) Patent No.: US 7,910,381 B2
(45) Date of Patent: *Mar. 22, 2011

(54) IMMUNO GOLD LATERAL FLOW ASSAY

(75) Inventors: Glen Ford, Montgomery Village, MD (US); Leslie Kirkegaard, Ijamsville, MD (US)

(73) Assignee: BioAssay Works, Ijamsville, MD (US)

( * ) Notice: Subject to any disclaimer, the term of this patent is extended or adjusted under 35 U.S.C. 154(b) by 414 days.

This patent is subject to a terminal disclaimer.

(21) Appl. No.: 12/073,435

(22) Filed: Mar. 5, 2008

(65) Prior Publication Data
US 2008/0188009 A1  Aug. 7, 2008

Related U.S. Application Data

(63) Continuation-in-part of application No. 11/512,148, filed on Aug. 30, 2006, now abandoned, which is a continuation-in-part of application No. 11/248,214, filed on Oct. 13, 2005, now Pat. No. 7,344,893.

(51) Int. Cl.
*G01N 33/53* (2006.01)

(52) U.S. Cl. ............. 436/514; 435/287.7; 435/805; 435/970; 435/967; 435/975; 436/518; 436/501; 436/512; 436/523; 436/536; 436/807; 422/56; 422/57; 422/58; 422/59; 422/60

(58) Field of Classification Search .......... 435/805, 435/967, 970, 975, 287.7; 436/514, 518, 436/501, 512, 523, 536, 807; 422/56, 57, 422/58.59, 60

See application file for complete search history.

(56) References Cited

U.S. PATENT DOCUMENTS

| 5,565,366 A | * | 10/1996 | Akers, Jr. .......... 436/534 |
| 5,602,040 A | * | 2/1997 | May et al. .......... 436/514 |
| 6,534,324 B1 | * | 3/2003 | Zin .......... 436/518 |

* cited by examiner

*Primary Examiner* — Bao-Thuy L Nguyen
(74) *Attorney, Agent, or Firm* — Jonathan Grant; Grant Patent Services

(57) ABSTRACT

A chromatographic specific binding assay strip device, comprising: a non-permeable platform strip; a permeable membrane testing strip positioned on top of said non-permeable platform strip, with the testing strip comprising at least one capture reagent site containing a capture reagent for at least one specific analyte, a sample receiving pad positioned on top of and at a proximal end of the non-permeable platform strip, with the sample receiving pad having contact with a proximal end of said permeable membrane testing strip, a reservoir pad positioned on top of and at a distal end of said non-permeable membrane testing strip, with the reservoir pad having contact with a proximal end of said permeable membrane test strip; a supporting strip attached to and extending from the proximal end of said non-permeable platform strip; and a conjugate pad positioned on said supporting strip, said conjugate pad comprising a semi-permeable membrane containing a colorant conjugate. The semi-permeable membrane acts as a barrier between the conjugate pad and the sample receiving pad, regulating the flow through the semi-permeable membrane and overall flow of the assay by dipping the conjugate pad into a sample solution, there will be increased binding between the analyte in the sample and the conjugate (preferably colloidal gold), thereby giving improved results on the lateral flow assay.

8 Claims, 9 Drawing Sheets

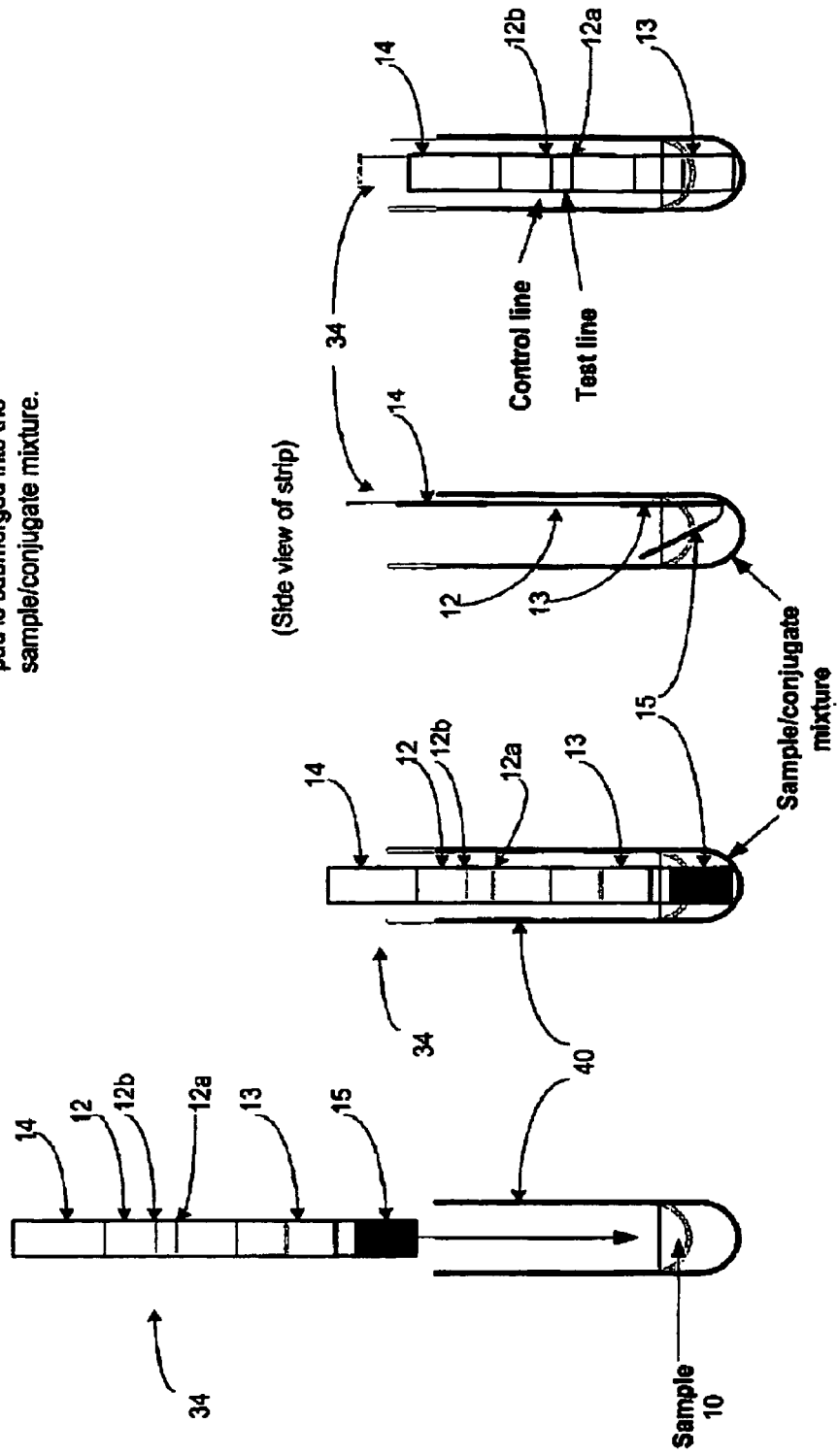

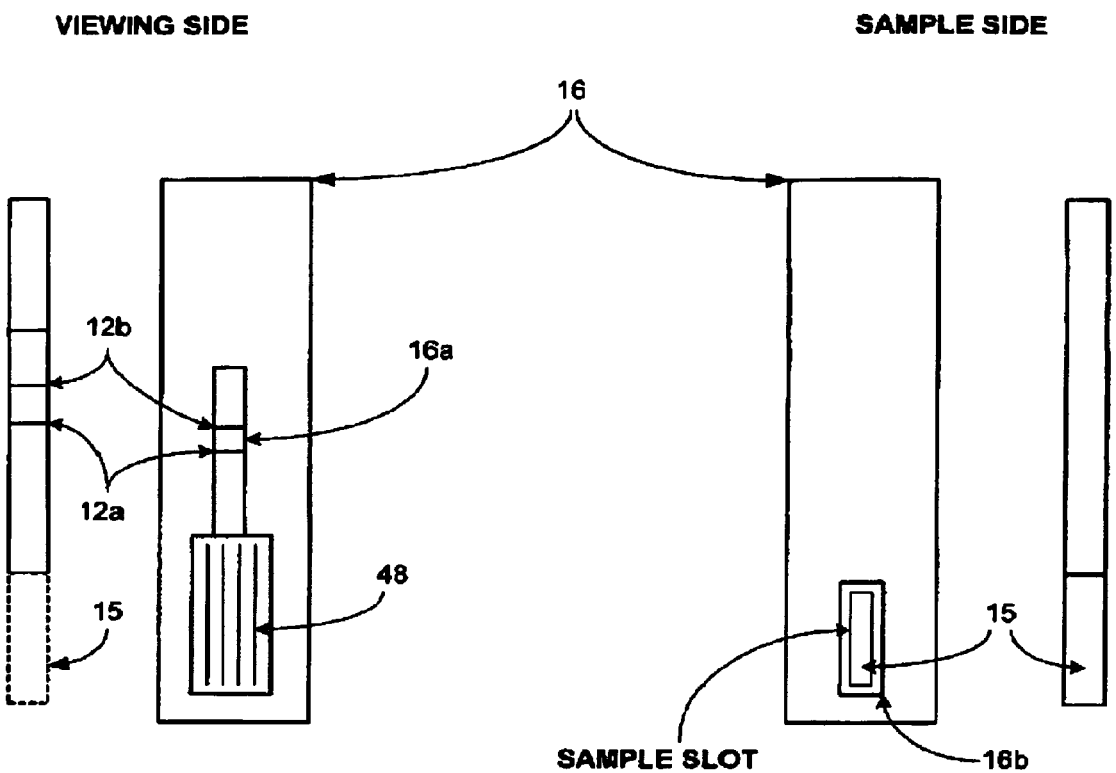
FIG. 5A  FIG. 5B
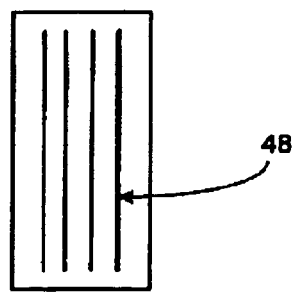
FIG. 6

1

IMMUNO GOLD LATERAL FLOW ASSAY

This application is a continuation-in-part of application Ser. No. 11/512,148, filed Aug. 30, 2006 now abandoned, which is a continuation in part of Ser. No. 11/248,214, filed on Oct. 13, 2005 now U.S. Pat. No. 7,344,893, and claims benefit of these earlier filing dates under 35 U.S.C. 120, the contents of which are herein incorporated by reference.

FIELD OF DISCLOSURE

The present disclosure generally relates to an assay system and apparatus involving specific binding of analytes and/or ligands, and specifically relates to chromatographic flow binding assays with a colored conjugate.

BACKGROUND OF THE DISCLOSURE

It is increasingly desirable to provide a rapid high sensitivity system to detect low levels of ligands in body fluids, plant extracts, environmental samples, tissue samples and enrichment broths. Ideally, such systems should have a minimal number of procedural steps and yield reliable results, even when used by untrained persons.

To a significant extent, many known tests presently available for detecting ligands are either time consuming, labor intensive, or in need of instrumental assistance to read results. Most known tests also lack an acceptable degree of sensitivity or specificity. This is unfortunate since rapid testing is important for diagnosis and treatment of various bacterial, fungal, and viral pathogens. Additionally, rapid testing can be used for detection of drug analytes, cancer cells, antibodies, disease-state protein, and the like.

Although known types of ligand-receptor assays have been used to detect the presence of various substances, such as ligands, there is a need in the art to provide a rapid, high sensitivity assay requiring a minimum degree of skill from a user. Rapid test assay devices for field use, such as in a home or doctor's office are known in the art for detecting proteins, peptides, drugs, carbohydrates, haptens, chemicals, chemical reaction with intermediate compounds, and the like. Such devices are referred to as one-step lateral flow or immunochromatographic assays. These types of assay devices require a minimal number of steps and can be performed by an untrained person.

Several one-step lateral flow immunoassay devices having a strip capable of transporting a developing liquid by capillary action having a first zone for receiving a sample, a second zone impregnated with a first reagent capable of being transported by the developing liquid, and a third zone impregnated with a second reagent, are known in the art.

U.S. Pat. Nos. 4,094,647 and 4,235,601 (Deutsch et al.) disclose a test device for determining a characteristic of a sample, particularly for determining substances in fluid samples. A strip element has a predetermined location for receiving the test sample and predetermined locations incorporated with reagent means for providing a detectable response sensitive to the characteristic under determination. The beginning end portion of the strip element is immersed in the developing fluid which, as a result, traverses the length of the strip element, thereby promoting appropriate contact between the test sample and the reagent means resulting in the disposition of a detectable response at a predetermined location on the strip element. The test device is particularly suited for performing binding assays, and in particular those wherein a radioisotope is used as a label, such as radioimmunoassays.

U.S. Pat. No. 6,352,862 (Davis et al) discloses an analytical test device incorporating a dry porous carrier to which a liquid sample can be directly applied. The device also incorporates a labeled specific binding reagent which is freely mobile in the porous carrier when in the moist state, and an unlabelled specific binding reagent which is permanently immobilized in a detection zone on the carrier material. The labeled and unlabelled specific binding reagents are capable of participating in either a sandwich reaction or a competition reaction in the presence of the analyte, in which prior to the application to the device of a liquid sample suspected of containing the analyte, the labeled specific binding reagent is retained in the dry state in a macroporous body, eg. of plastics material having a pore size of 10 microns or greater, through which the applied liquid sample must pass en route to the porous carrier material, with the labeled specific binding reagent being freely soluble or dispersible in any liquid sample which enters the macroporous body.

U.S. Pat. No. 5,120,643 (Ching et al.) relates to improved specific binding assay methods, kits and devices utilizing chromatographically mobile specific binding reagents labelled with colloidal particles. Specific binding reagents labelled with colloidal particles such as gold and selenium may be subjected to rapid chromatographic solvent transport on chromatographic media by means of selected solvents and chromatographic transport facilitating agents. Further, impregnation of solid substrate materials with labile protein materials including colloidal particle and enzyme labelled reagents in the presence of meta-soluble proteins provides for the rapid resolubilization of such materials which have been dried onto such substrate materials.

A major disadvantage of all of the known prior art is that the majority of sample applied to a lateral flow assay is not involved in the immunological reaction. For example, between 10 .mu.l to 20 .mu.l of sample is all that is required to fully rehydrate a 5 by 5 mm gold pad or membrane with the conjugate pad or membrane composed of polyester, glass, nylon, cellulose or other fibers. Since the conjugate pad or membrane is in the device flow path and in contact with the membrane, a minimal remaining sample is involved in the immunological reaction. The remaining 50 .mu.l to 150 .mu.l of sample acts as a liquid front by pushing the reacted analyte conjugate complexes through the flow path. Since only 10 to 20 microliters of sample is involved in the reaction, only a few analyte molecules of interest in the sample are bound to the colloidal conjugate, thus limiting the number of molecules involved in the immuno-chromatographic reaction. Thus, a severe limitation of the one-step lateral flow assay is the limited amount of sample actually involved in the reaction with the conjugate.

Further, in a one-step lateral flow assay, as a sample mixes with a dry conjugate, incomplete mixing often yields conjugate particles with vastly different numbers of captured analyte molecules. This alone may be a source of decreased sensitivity since the maximum number of analyte molecules are not captured on the surface of the conjugate particles.

Other designs are known in the art also include two-step assays. These assays often require the conjugate pad or membrane to be physically and spatially removed from the test strip. For example, there are assays known in the art where the conjugate is contained in book form, or a "male to female" molded apparatus. In the book form, the test strip is located on one panel of the book while the conjugate is located on the other panel. The test requires the user to close both halves for the test to begin. With the "male to female" apparatus, the sample is applied to the male portion of the apparatus, and the two halves are closed to initiate the reaction. Another format has the conjugate dried and located on a separate sampling stick. The sampling stick is mixed with a sample and is then fixed in the cassette sample well. For example, some two step assay platforms are known in the art, such as indicated in U.S. Pat. No. 6,824,997 and U.S. Pat. No. 5,418,171.

These tests have a significant drawback though. The end user must perform an additional step to physically bring the membrane and conjugate into contact after the sample has been adequately mixed. Sometimes, the sample "swamps" the assay, making the results hard to read.

Thus, there is a desire and need in the art for a high sensitivity assay system and apparatus to rapidly detect low levels of ligands in a small sample size of fluid. Such new tests should involve a minimal number of procedural steps while at the same time, yielding reliable results, even when used by untrained persons.

SUMMARY OF THE DISCLOSURE

The present disclosure teaches a rapid high sensitivity system apparatus and method for detecting low levels of ligands in body bio-fluids, environmental and tissue culture extracts, with high sensitivity and specificity. The disclosure generally relates to a rapid, high sensitivity chromatographic assay for detecting low levels of ligands in bio-fluids, environment, plant and tissue culture extracts, using a minimal number of procedural steps even when used by untrained persons, and can encompass diagnostic kits that may contain a chromatographic specific binding assay system, and preferably an immunochromatographic specific binding assay system. Furthermore, the system and apparatus, because of its accuracy and simple method steps, make it appropriate for field use such as a home, clinic, point of care setting, or doctor's office. Test results may be visually read or read by an instrument known in the art and readily available to give either a semi-qualitative (e.g., a positive/negative result) or a quantitative result. In use, the present invention is simple to use and requires a minimum degree of user skill and involvement.

For the purposes of this disclosure, the term ligand may include but is not limited to a specific sequence of amino acids or molecule found on proteins such as an antibody, protein receptors, bacterial/microbial peptides, hormone, or drug that binds to a receptor. A receptor, is any of various specific protein molecules in surface membranes of cells and organelles to which complementary molecules, such as hormones, neurotransmitters, antigens, or antibodies, may become bound. The ligand may also be a chemical intermediate or reactant with an analyte. Analytes are substances that bind to a ligand, or may be part of the ligand. Ligands or analytes may also be peptides, drugs, carbohydrates, haptens, chemicals, chemical reaction with an intermediate compound, and the like. Other substances may also be ligands.

In one embodiment of the disclosure, a chromatographic specific binding assay strip device is disclosed, comprising: a non-permeable platform strip, a permeable membrane testing strip positioned on top of the non-permeable platform strip, a sample receiving pad positioned on top of and at a proximal end of the non-permeable platform strip while in contact with the proximal end of the permeable membrane testing strip, a reservoir pad positioned on top of and at a distal end of the non-permeable membrane testing strip while in contact with the distal end of the permeable membrane test strip; a conjugate pad membrane attached to and extending from the proximal end of the non-permeable platform strip, and a conjugate pad positioned on said conjugate pad membrane, said conjugate pad comprising a permeable membrane containing a colorant conjugate.

Using the above described assay strip, a sample or diluent thereof is prepared and poured into a test tube. Next, the conjugate pad of the lateral flow assay, preferably containing conjugated colloidal gold, is inserted into the sample in the test tube. It is most preferable if the tube is gently shaken, to encourage complete mixture of all of the sample and all of the conjugate gold. After about five to twenty seconds, or any fair amount of time to allow the ligand in the sample the conjugate gold to mix and bind, the assay strip is further pushed into the test tube so that the sample receiving pad is in contact with the colloidal gold coated ligand sample. Capillary action will then draw the gold coated ligand sample along the path of the lateral flow assay, and a positive result will show up at a line at the site of the appropriate anti-ligand antibody. The lateral flow assay can be withdrawn from the sample liquid after 5-15 seconds and placed in a horizontal position, or the lateral flow assay can remain in the sample liquid during the time that the sample is being drawn up by capillary action.

In the use of the lateral flow assay described above, it does not matter whether or not the conjugate pad is on top or on bottom of the conjugate pad membrane. However, in some circumstances, particularly when a plastic cassette case is used to hold the lateral flow assay strip, it may be preferable to have the conjugate pad on the underside of the conjugate membrane.

In another embodiment of the disclosure, a chromatographic specific binding assay strip device is disclosed, comprising: a non-permeable platform strip, a permeable membrane testing strip positioned on top of the non-permeable platform strip, a sample receiving pad positioned on top of and at a proximal end of the non-permeable platform strip while in contact with the permeable membrane testing strip, a reservoir pad positioned on top of and at a distal end of the non-permeable membrane testing strip while in contact with the permeable membrane test strip; a semi-permeable membrane positioned on top of said sample pad; and a conjugate pad positioned on top of said semi-permeable membrane, said conjugate pad comprising a permeable membrane containing a colorant conjugate.

A semi-permeable membrane, is a membrane which will allow certain molecules or ions to pass through it by diffusion and occasionally specialized "facilitated diffusion". The rate of passage depends on the pressure, concentration, and temperature of the molecules or solutes on either side, as well as the permeability of the membrane to each solute. Depending on the membrane and the solute, permeability may depend on solute size, solubility, properties, or chemistry. An example of a semi-permeable membrane is a lipid bilayer, on which is based the plasma membrane that surrounds all biological cells. Many natural and synthetic materials thicker than a membrane are also semi-permeable. An example of this is the thin film on the inside of an egg.

Another example of a semi-permeable membrane is a phospholipid bilayer, a group of phospholipids (consisting of a phosphate head and 2 fatty-acid tails) arranged into a double-layer, with the hydrophilic phosphate heads exposed to the water content outside and within the cell and the hydrophobic fatty-acid tails hidden in the inside. The phospholipid bilayer is the most permeable to small, uncharged solutes. Protein channels float through the phospholipids, and collectively, this model is known as the fluid mosaic model.

In the process of reverse osmosis, thin film composite membranes (TFC or TFM) are used. Thin film composite membranes are semi-permeable membranes manufactured principally for use in water purification or desalination systems. They also have use in chemical applications such as batteries and fuel cells. Essentially, a TFC material is a molecular sieve constructed in the form of a film from two or more layered materials.

Membranes used in reverse osmosis are typically made out of polyimide, chosen primarily for its permeability to water and relative impermeability to various dissolved impurities including salt ions and other small molecules that cannot be filtered. Another example of a semi-permeable membrane is dialysis tubing.

In this arrangement, the sample to be tested is added to the conjugate pad, which, of course, rests on top of the semi-permeable pad which in turn sits astride the sample pad. The semi-permeable pad is restrictive, and slows down the flow of the conjugate sample, thereby increasing the amount of time the conjugate reacts with the ligand or analyte, giving clearer, more defined, results.

The semi-permeable pad may sit directly on top of the sample pad, or it may be attached to the impermeable membrane with the conjugate pad positioned on the underside of the semi-permeable pad. That way, the semi-permeable pad can be flipped up so that the conjugate pad, is on top of the semi-permeable pad when the sample is added.

It should be note that the semi-permeable membrane, also termed a selectively permeable membrane, a partially permeable membrane or a differentially permeable membrane, is a membrane which will allow certain molecules or ions to pass through it by diffusion and occasionally specialized "facilitated diffusion". The rate of passage depends on the pressure, concentration and temperature of the molecules or solutes on either side, as well as the permeability of the membrane to each solute. Depending on the membrane and the solute, permeability may depend on solute size, solubility, properties, or chemistry. An example of a semi-permeable membrane is a lipid bilayer, on which is based the plasma membrane that surrounds all biological cells. Many natural and synthetic materials thicker than a membrane are also semi-permeable. An example of this is the thin film on the inside of an egg.

One example of a semi-permeable membrane is a phospholipid bilayer, a group of phospholipids (consisting of a phosphate head and 2 fatty-acid tails) arranged into a double-layer, with the hydrophilic phosphate heads exposed to the water content outside and within the cell and the hydrophobic fatty-acid tails hidden in the inside. The phospholipid bilayer is the most permeable to small, uncharged solutes. Protein channels float through the phospholipids, and collectively, this model is known as the fluid mosaic model.

In the process of reverse osmosis, thin film composite membranes (TFC or TFM) are used. Thin film composite membranes are semi-permeable membranes manufactured principally for use in water purification or desalination systems. They also have use in chemical applications such as batteries and fuel cells. Essentially, a TFC material is a molecular sieve constructed in the form of a film from two or more layered materials.

Membranes used in reverse osmosis are typically made out of polyimide, chosen primarily for its permeability to water and relative impermeability to various dissolved impurities including salt ions and other small molecules that cannot be filtered. Another example of a semi-permeable membrane is dialysis tubing.

The membrane may also be constructed of hydrophobic material allowing for the slow diffusion of sample mixed with conjugate through the semi-permeable membrane In another embodiment of the disclosure, the liquid migration is regulated or adjusted by the porous nature of the semi-permeable piercing the laminating membrane, or by using a laminate with hatched fibers creating with micropores.

In yet another embodiment of the disclosure, a cassette housing in a sample well or opening receives the liquid sample. The cassette contains ridges or channels designed to both pre-mix the sample with conjugate, and to facilitate a unidirectional flow path. The sample port is on the same side of the same plane of the test cassette as the visualization window.

In yet another embodiment of the disclosure, the colloidal gold conjugate is blocked with bovine serum albumin (BSA) and detergents which are used for preventing loss of antibody by non-specific attachment to the colloidal gold surface.

In a further embodiment of the disclosure the binding assay strip is an immunological binding assay strip.

A further embodiment of the disclosure comprises a buffered diluent and wherein the conjugate is a colloidal metal.

The lateral flow assay device may be in a kit which includes a buffered diluent, wherein the conjugate is a colloidal metal.

In one embodiment of the disclosure, a (e.g., positive/negative) indicator, such as the presence of agglutination or a color change, as well as quantitative determination, is taught.

In another embodiment of the disclosure, a membrane strip is taught that increases detection on the order of 2 to 10 fold over the conventional chromatographic specific binding assay techniques. By placing a dried or lyophilized colloidal sphere conjugate in a sample solution, as occurs when the conjugate extends or protrudes from the end of the strip and is added to a test tube containing sample, this then allows for more complete binding of the colorant to the targeted ligands of the solution, since the sample and conjugate come to a homogenous mixture prior to the start of the reaction.

In another version of the disclosure, a semi-permeable material over the sample pad or membrane serves as a temporary obstruction, impeding the flow of a sample solution, thereby resulting in the sample and conjugate label being in contact for a longer amount of time before flowing out of the conjugate pad.

Yet another embodiment of the disclosure suggests the inclusion of a novel conjugate pad or membrane solution dried onto the conjugate pad or membrane. This solution is composed of negatively charged detergents that are coated onto the conjugate pad or membrane. When the sample contacts a conjugate pad or membrane, the labeled colored particles are rapidly expressed into the sample where the test ligand has an increased opportunity to react with said conjugate particles.

In yet another embodiment of the disclosure, several cassettes are used, designed to allow for sample loading either on the reverse of the cassette, the cassette side, or on the front of the cassette for use with the test strip. When loading the sample on the front or side of the cassette, the cassette contains ridges or channels designed both to transport the sample directly to the conjugate pad or membrane and to pre-mix the sample and conjugate.

None of the known prior art teach or suggest locating the conjugate pad or conjugate impregnated membrane on the reverse side of the strip and bound to a the semi-permeable membrane, and not in contact with either the sample receiving pad or the membrane. By locating the conjugate pad or membrane on the reverse side of the membrane, and then folding over the conjugate pad such that the semi-permeable membrane separates the conjugate pad from the sample receiving pad, the entire sample first rehydrates the conjugate resulting in a uniform dispersion of conjugate through the entire applied sample. In the test tube version, the semi-permeable membrane is attached to the conjugate such that it protrudes from the end of the strip. In this case, the conjugate is not folded over as in claim 1. This allows for the conjugate to mix with the sample contained in a test tube prior to the start of the capillary flow. The flow does not start until the strip is pushed fully into the test tube in order to capture on the sample receiving pad the liquid mixture of sample and conjugate. In the test tube version, the strip may also be contained in a mini-cassette with the conjugate protruding from the end of the strip. The cassette is able to fit into a wider test tube of appropriate diameter.

Additional aspects and advantages of the invention will become apparent from the following detailed description, the drawings, and the appended claims.

BRIEF DESCRIPTION OF THE FIGURES

The foregoing features, as well as other features, will become apparent with reference to the description and figures below.

FIG. 4 is a view of the lateral flow assay being used to test a sample in the test tube;

FIGS. 5*a* and 5*b* provide direct and side views of the cassette;

FIG. 6 is another view of part of the cassette;

DETAILED DESCRIPTION OF THE DISCLOSURE

Figure 1A:
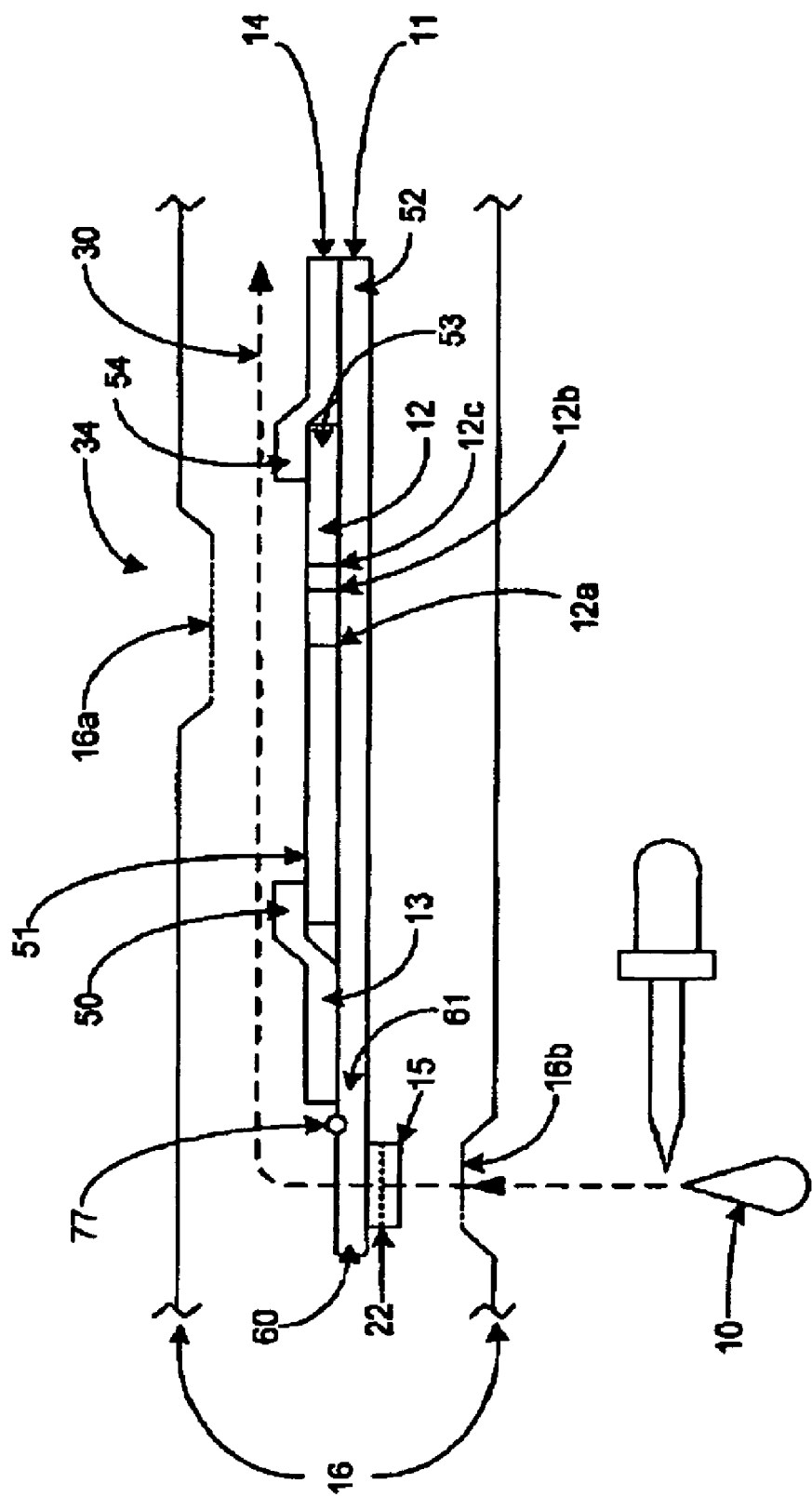
FIGS. 1*a*-1*c* are side views of a chromatographic assay device.

Referring to FIGS. 1-4, the lateral flow assay device 34 is comprised of a platform strip 11. It is preferred that the platform strip 11 be impermeable, and, preferably, laminated, and to that end, a plastic platform strip may be used. The platform strip 11 is elongated. Positioned on the top side of the platform strip 11 is a permeable membrane testing strip 12, where the sample/conjugate mixture can bind or stick to the immobilized capture reagent, causing a color reaction, indicating the presence of a specific ligand or analyte. The presence and/or amount of analyte in the sample 10 may be determined by the visibility of a line formed by the capture reagent 12*a*, specific for the analyte-label reagent conjugate being tested. There may be more than one capture reagent and more thus more than one capture reagent site when a multiple of analytes are being (possibly) be tested and examined. It is also preferred that there be a control reagent 12*b*, which is used to verify that the test is not giving any false positives or false negatives (depending on how the control is constructed). There may also be a second control region 12*c* so that there may be both a negative and a positive control. The platform strip gives "body" and strength to the longitudinally positioned testing strip. The permeable membrane testing strip, which could be more properly called an detection membrane strip 12 may be composed of a series of porous material pieces such as, paper, cotton, polyester, glass, nylon, mixed cellulose esters, spun polyethylene, polysulfones, and the like. Preferably, nitrocellulose, nylon or mixed cellulose esters are used for the analyte detection membrane strip 12. It can be attached to the platform strip by any number of means, including a variety of simple glues or tape, as long as the glues do not permeate up through and to the surface of the permeable membrane testing strip 12.

A sample receiving pad 13 is positioned on top of and at a proximal end of the non-permeable platform strip 11 while in contact with the permeable membrane testing strip 12. More specifically, the distal end 50 of the sample receiving pad 13 should either be in physical contact with the proximal end 51 of the permeable membrane testing strip 12 or the distal end 50 of the sample receiving pad 13 should be in contact with and overlap the proximal end 51 of the sample receiving pad 13. The sample receiving pad 13, may be composed of a series of porous material pieces such as, paper, cotton, polyester, glass, nylon, mixed cellulose esters, spun polyethylene, polysulfones, and the like. Preferably, paper, cotton, polyester, glass fiber, or polyethylene are preferred for the sample receiving pad.

A reservoir absorbent pad 14 is positioned on top of and at a distal end 52 of the non-permeable membrane platform strip 11 while in contact with the distal end 53 of the permeable membrane test strip 12. It is preferred that the proximate end 54 of the reservoir absorbent pad 14 overlaps the distal end 53 of the permeable membrane test strip 12. The reservoir absorbent pad 14 helps draw the fluid sample across the permeable membrane testing strip 12 by capillary action. The reservoir pad may be composed of a series of porous material pieces such as, paper, cotton, polyester, glass, nylon, mixed cellulose esters, spun polyethylene, polysulfones, and the like. Preferably, the reservoir absorbent pad 14 is comprised of paper, cotton, polyester, glass fiber, or polyethylene.

A semi-permeable membrane "tail" 60 is attached to the proximal end 61 of the non-permeable platform strip 11. In one embodiment of the disclosure, a conjugate pad 15 resides on the underside of the semi-permeable membrane. In another embodiment, the semi-permeable membrane 60 resides directly on top of the sample receiving pad 13, and the conjugate pad 15 resides on top of the semi-permeable membrane. In other embodiments, it does not make a difference as to whether the conjugate pad is placed on top of the semi-permeable membrane, or whether the conjugate pad is on top of or below the semi-permeable membrane when said semi-permeable membrane is attached to the platform strip. The semi-permeable membrane is constructed of micropores of diameters between 0.01 microns and 10 microns, allowing the sample to slowly diffuse through the semi-permeable membrane. The semi-permeable membrane may also be constructed of hydrophobic material or hatched fibers creating micropores, thus allowing for the slow diffusion of sample mixed with conjugate through the semi-permeable membrane.

It should be noted that in some embodiments of the disclosure, where not needed, the "tail" need not be a semi-permeable membrane, but instead could be permeable or non-permeable.

In another embodiment of the disclosure, the conjugate pad 15 may be attached directly to an extension 70 at the proximal end of the non-permeable platform strip 11, by the usual, known methods of attachment, some of which were discussed above. The conjugate pad may be added in any number of ways and shapes, and shown in FIGS. 2*a*-2*c*.

The conjugate pad itself 15 is comprised of paper, cotton, polyester, glass fiber, or polyethylene. More importantly than the material of the conjugate pad are the lyophilized colorants in the pad. The dried or lyophilized conjugate 22 in the conjugate membrane 15 may consist of latex microparticles, enzymatic, fluorescent, or visually observable tags. These other tags include metal sols, enzymatic, fluorescent, latex microparticles, and the like, preferably colloidal gold particles. The purpose of the conjugate 22 is to provide a means of identifying any reaction or binding at the site of the capture reagent 12a. These means can include visual, fluorescence, radioactive, etc.

Figure 3:
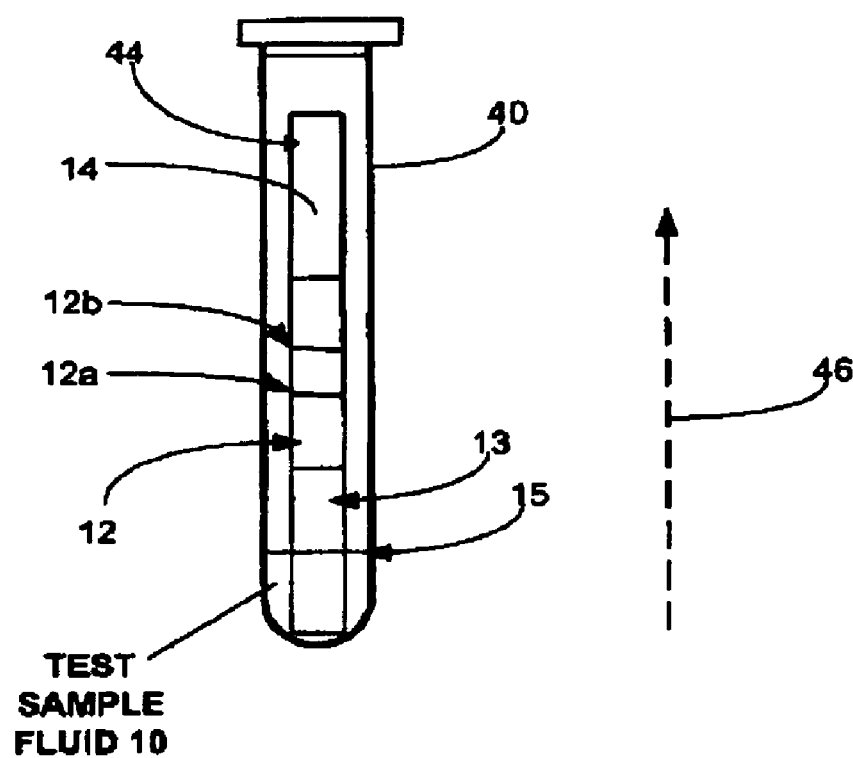
FIG. 3 is an exploded view of one version of the test strip being exposed to a sample fluid in a test tube.
Figure 7:
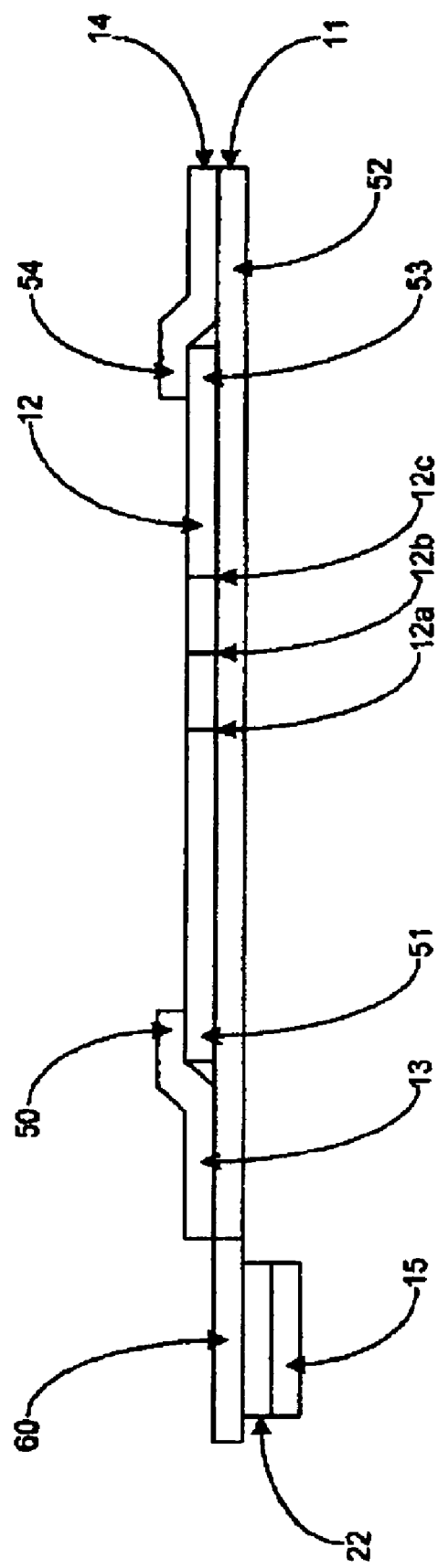
FIG. 7 is a side view of another embodiment of the device.

One embodiment of the present disclosure allows the chromatographic test assay to be performed in a test tube 40 containing a liquid sample as shown in FIG. 3. In the test tube version, the unfolded semi-permeable membrane 60, to which the conjugate pad 15 is attached, is dipped into a sample solution 10 in the test tube, thereby allowing the conjugate to mix with the sample contained in a test tube prior to the start of the capillary flow along the path of the test strip. By inserting the extended semi-permeable membrane 60 or, more simply, by submerging the entire conjugate pad 15 residing on the semi-permeable membrane 60 into the liquid sample solution 10, all of the dehydrated or lyophilized conjugate is rehydrated and the entire sample (usually between 100 and 250 microliters) is exposed to, and gently mixed with the entire conjugate. This process allows for a five to 20 fold increase in the formation of analyte-conjugate complexes over the prior art. Every analyte molecule in the sample is bound to the colloidal conjugate, thus significantly increasing the number of molecules involved in the immuno-chromatographic reaction. Each conjugate particle contains a uniform number of captured analyte molecules, and further each conjugate particle contains about the same number of captured analyte molecules. While it is preferred that the membrane be semi-permeable, for this use of the test tube assay test, the membrane may be permeable or non-permeable. In fact, a membrane may not necessary be needed at all, but a platform (such as the plastic laminate 11) could be used to support and hold the conjugate pad.

The diluent may be composed of salt solutions, detergents, and the like and may be applied from a dropper tip vials or contained in a sample vial.

It should be noted that sample size is determined by the capacity of the wick pad 14 and may be as much as 500 .mu.l compared to 10 .mu.l to 20 .mu.l of effective sample 10 as constrained by one-step lateral flow assays in the prior art.

The capillary flow along the test strip 12 does not begin until the lateral flow assay device 34 is pushed into the test tube such that the sample receiving pad 15 is fully exposed to the sample solution which is now comprised of conjugate bound analyte. The assay test 34 can remain in the test tube or it can be removed and placed horizontally, with the test strip face up.

As the now conjugated sample 10 migrates into the flow membrane, the analyte-particle conjugate is carried along flow path 46 where it is given opportunity to react with the capture analyte attached to the analyte detection membrane 12 at site 12a.

The site of capture may be an antibody specific for a particular analyte, antigen, antibody, protein, carbohydrate, or any other biological or chemical structure. Alternatively, the capture site a capture may be an analyte, antigen, antibody, protein, carbohydrate or another biological structure, and the sample may include the target antibody.

In one embodiment of the present disclosure, the immunoreactive protein may be a ligand to which antibodies contained in positive sample 10 reacts with such as HIV, HTLV, TB, and the like. Detection membrane strip 12 may be impregnated with anti-antibody to capture total, class and subclass immunoglobulins. In this case, the specific antibody in sample 10 reacts with ligand peptides (HIV, HTLV, TB, and the like) coated onto the surface of the particles 22.

In another embodiment of this invention, device 34 may have antigen on both the conjugate pad and membrane 15. The analyte detection membrane strip 12 surfaces to which specific antibody may then be able to react with separate binding domains on the antibody. If analyte detection membrane strip 12 is detecting antigen as the analyte, the membrane 12 surface may be impregnated with antibody or ligand reactive with the antigen. Typical antigen capture examples are specific antigen peptides, HIV p24 antigen, Hepatitis B surface antigen, cardiac markers, bacterial cells and the like and are known in the art. A colored line formed in this area may indicate detectable levels of analyte. A control zone, which indicates to the user whether or not the test was successfully run may also be included and illustrated in figures. In this example, the control in region 12b reacts with the conjugate. Often, for human samples, the control line is an antibody fragment, such as Fragment antigen binding (FAB) '2 goat anti human IgG (H&L) from Jackson Immunoresearch or KPL. (FAB)'2 has two antigen-binding arms that remain linked. Using FAB material prevents the binding of the protein A coated gold particles 22, and indicates the addition of human sample 10 (containing antibody). If buffer alone is added to the test strip, no control line develops resulting in an invalid assay. A colored conjugate to which purified proteins, haptens, or antibody to human immunoglobulins is chemically attached. The dried or lyophilized conjugate 22 on the conjugate pad or conjugate membrane 15 is mixed with special solubilizing and releasing compounds in a buffer; facilitating any interaction with the sample 10 bio-fluid The analyte detection membrane 12 and sample receiving pad or membrane 13 and conjugate pad or membrane 15 may optionally contain bovine serum albumin (BSA) and detergents which act as effective blockers to prevent loss of human antibody, other ligands, haptens, proteins or analytes, by non-specific attachment to either the membrane or colored conjugate or both.

Figure 1B:
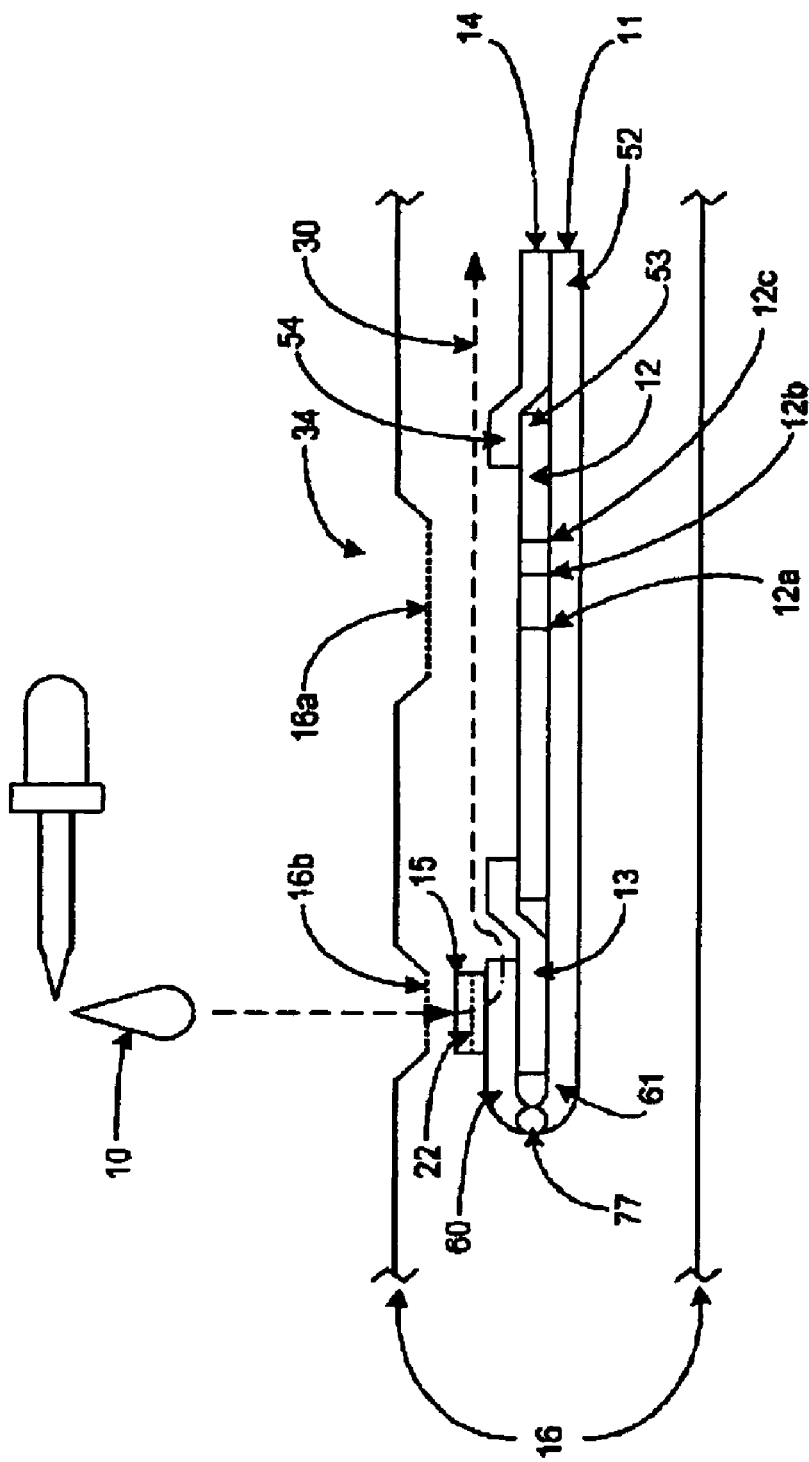
Figure 1C:
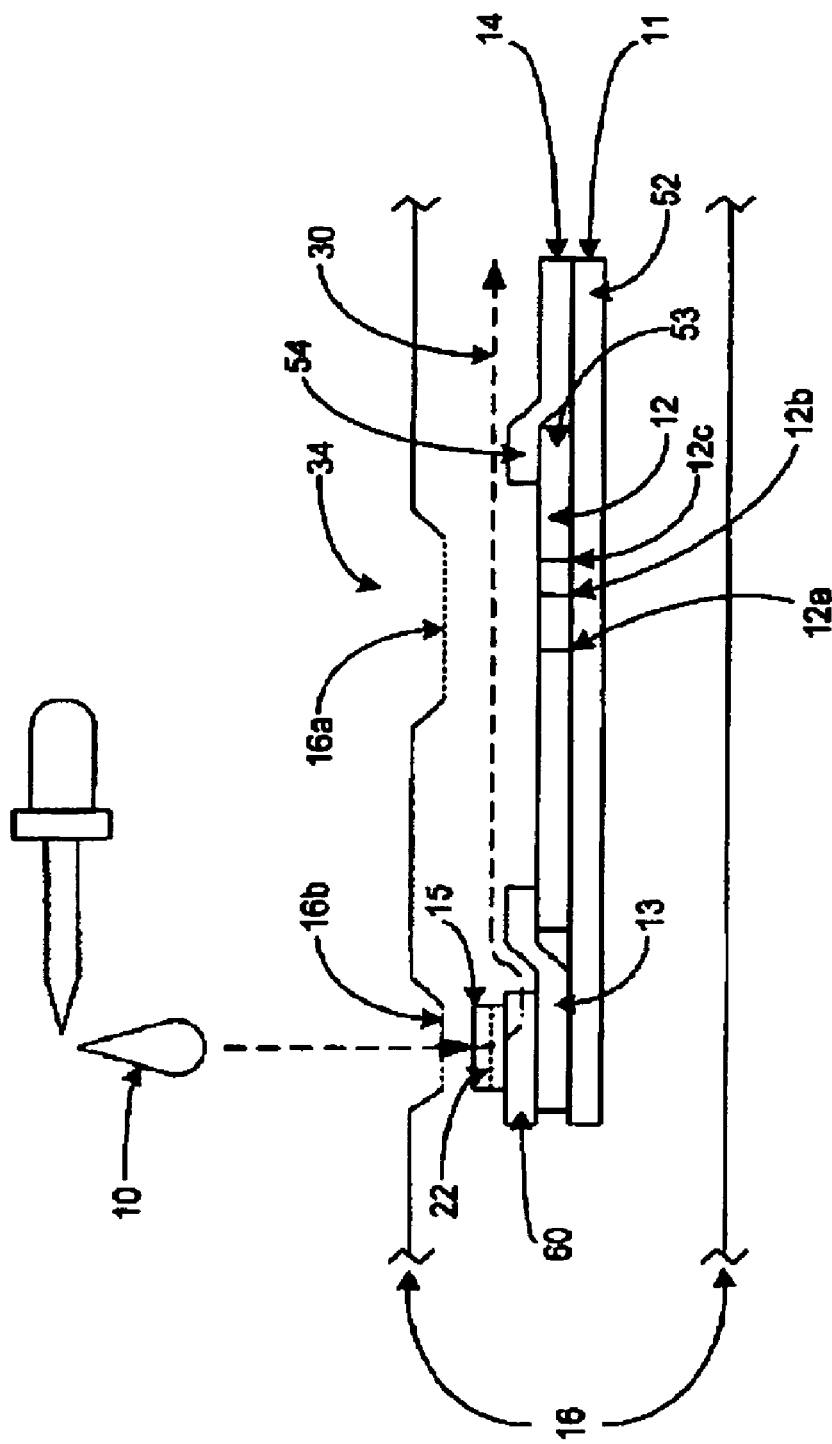
Figure 2A:
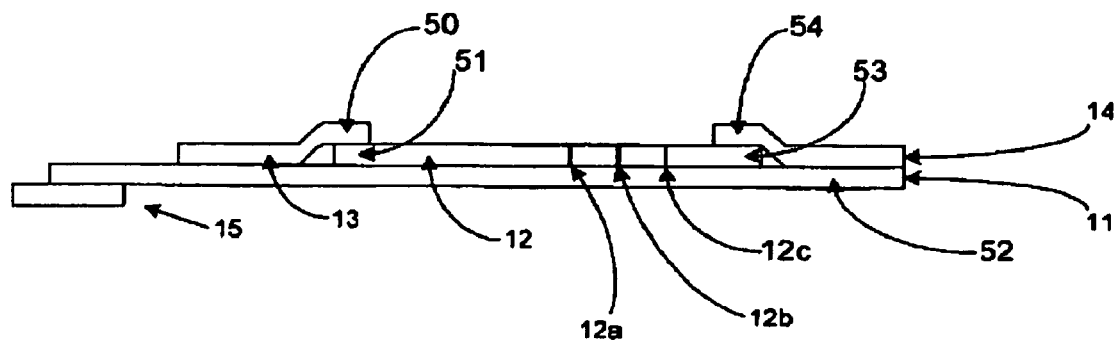
FIGS. 2*a*-2*c* are side views of another embodiment of the disclosure showing a conjugate pad attached to an impermeable platform strip.
Figure 2B:
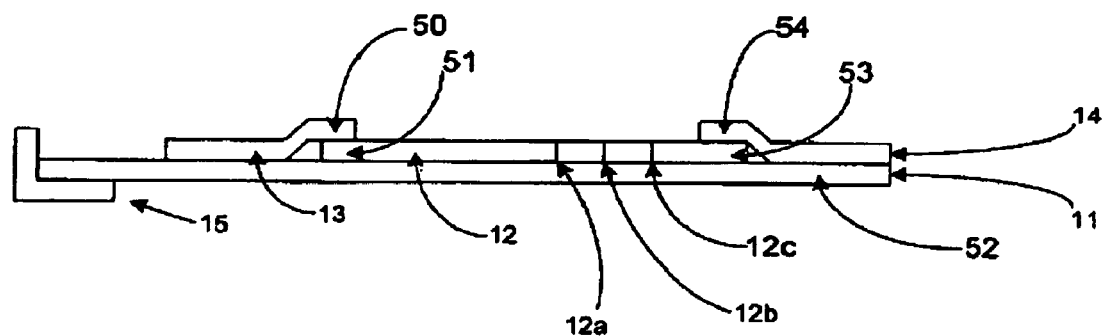
Figure 2C:
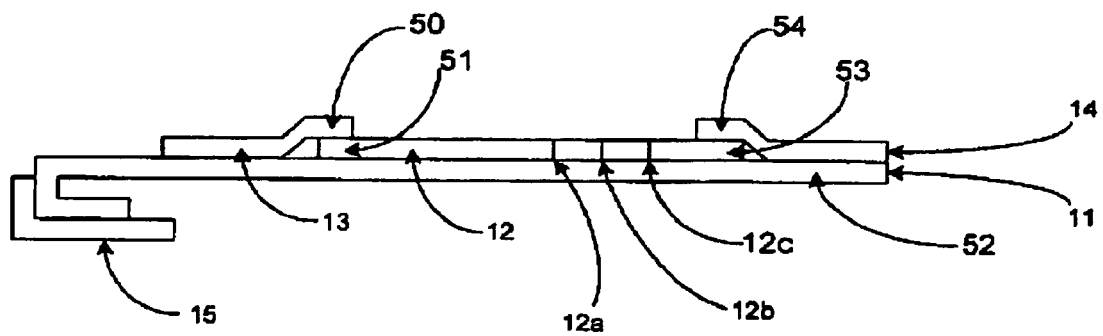
Figure 2D:
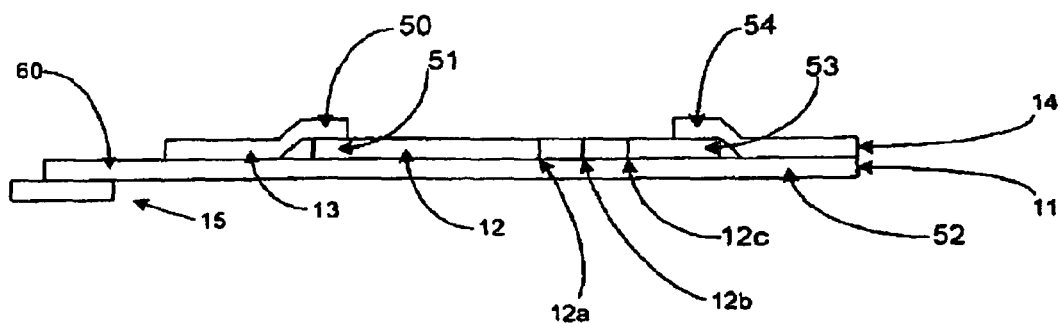
FIGS. 2*d*-2*f* are side views of another embodiment of the disclosure.
Figure 2E:
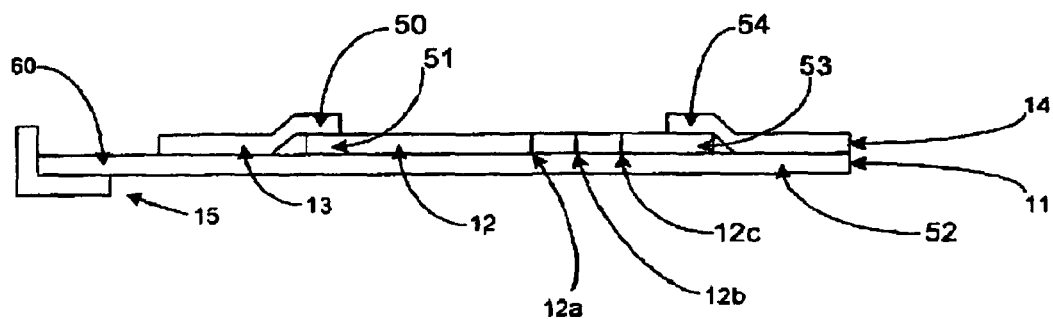
Figure 2F:
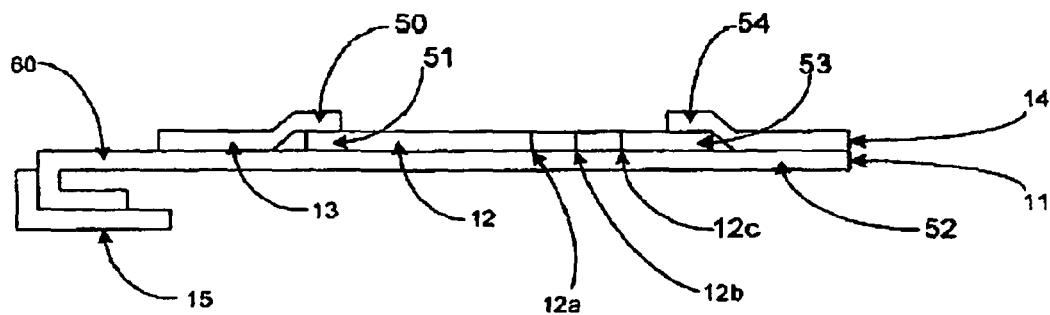

It should be noted that there are a number of different ways in which to attach the conjugate pad to the assay test. FIG. 1a shows a design where sample-conjugate pad 15 is located in a displaced position on the back side of semi-permeable membrane 60 which is attached to the non-permeable platform strip 11. The Figure also shows a hinge-point or region 77, to which semi-permeable membrane "tail" 60 is attached, so that the semi-permeable membrane 60 can be folded to result in the embodiment shown in FIG. 1b. This embodiment places conjugate pad 15 over the semi-permeable membrane 60 which is positioned over sample receiving pad 13 such that when sample is directly applied to the conjugate pad as shown in FIG. 1b or 1c, the fluid flow of the sample is slowed or impeded by the semi-permeable membrane 60, thereby facilitating or assisting in a more thorough or complete mixing of the conjugate and sample solution before it enters sample pad 13. This temporary obstruction breaks down when the combined effects of the sample volume and surface tension cause the sample to run eventually through semi-permeable membrane laminating membrane 11. The extended mixing permitted by this temporary obstruction is an important feature of the present disclosure providing the sample liquid and conjugate label to be in contact with each other for a longer amount of time before flowing into sample pad 13. Hatched fibers may be used in semi-permeable membrane 60 creating micropores. The extended of the analyte and the conjugate results in greater analyte detection sensitivity and is a salient difference over the prior art that gives the 2-step test its superior performance.

In another embodiment, as shown in FIG. 1c, the lateral flow assay is comprised of a non-permeable platform strip, a permeable membrane testing strip positioned on top of the non-permeable platform strip, and a sample receiving pad positioned on top and at a proximal end of the non-permeable platform strip while in contact with a proximal end of the permeable membrane testing strip. The reservoir pad is positioned on top of and at a distal end of the non-permeable membrane testing strip while in contact with a distal end of the permeable membrane test strip. A semi-permeable membrane is positioned on top of the sample pad, and a conjugate is positioned on top of the semi-permeable membrane. The conjugate pad itself is comprised of a permeable membrane containing a conjugate.

It should also be noted that the flow of fluid along the lateral flow assay 34 is reduced, which also aid in the reading of the results. The detection site 12a is not overwhelmed by a volume of fluid which may inadvertently washout some of the antibody or other detection means at site 12a.

In another embodiment of the disclosure, the assay testing device is in a cassette 16 as shown in FIG. 6a and FIG. 6b. The purpose of the cassette is to merely hold the assay testing device 34 in place. The test strip contains the conjugate pad folded or placed on top of the semi-permeable membrane. A liquid sample 10 can be applied through holes (cassette 16 openings) 16b onto a sample receiving pad or membrane 13. The sample fluid 10 flows out of the sample receiving pad or membrane 13 toward an adjacent dried or lyophilized conjugate pad 15. The dried colored conjugate pad is on top of a semi-permeable membrane and is subsequently rehydrated by the sample. After a period of time, the conjugate-sample complexes pass through the semi-permeable membrane and travel along a flow path 20. Detection may be observed through a viewing window area 16a of cassette 16 having a transparent cover.

The entire disclosure of each document cited (including patents, patent applications, journal articles, abstracts, laboratory manuals, books, or other disclosures) in the specification is hereby incorporated herein by reference.

While the invention has been described in conjunction with specific embodiments, it is evident that many alternatives, modifications and variations will be apparent to those skilled in the art in light of the foregoing description. Accordingly, the present invention attempts to embrace all such alternatives, modifications and variations that fall within the spirit and scope of the appended claims.

What we claim is:

1. A chromatographic specific binding assay strip device is disclosed, comprising:
    a) a non-permeable platform strip;
    b) a permeable membrane testing strip positioned on top of the non-permeable platform strip, said permeable membrane testing strip comprising at least one capture reagent site specific for an analyte being tested;
    c) a capture reagent positioned at each of said at least one capture reagent site
    d) a sample receiving pad positioned on top of and at a proximal end of the non-permeable platform strip while in contact with a proximal end of the permeable membrane testing strip
    e) a reservoir pad positioned on top of and at a distal end of the non-permeable membrane testing strip while in contact with a distal end of said permeable membrane test strip;
    f) a semi-permeable membrane positioned on top of said sample pad; and
    g) a conjugate pad positioned on top of said semi-permeable membrane, said conjugate pad comprising a permeable membrane containing a conjugate.

2. The chromatographic specific binding assay strip device according to claim 1, wherein said reservoir pad is fibrous.

3. The chromatographic specific binding assay strip device according to claim 1, wherein said conjugate of said conjugate pad is selected from the group consisting of latex microparticles, enzymatic, fluorescent, metal sols, and colloidal gold particles.

4. The chromatographic specific binding assay strip device according to claim 3, wherein said conjugate of said conjugate pad is a colloidal gold.

5. The chromatographic specific binding assay strip device according to claim 1, wherein said binding assay strip device is enclosed in a cassette, said cassette having an opening to view results of a test of a sample.

6. The chromatographic specific binding assay strip device according to claim 1, further comprising a control site on the permeable membrane testing strip.

7. The chromatographic specific binding assay strip device according to claim 1, wherein said device contains blocked bovine serum albumin and detergent to prevent loss of antibody, by non-specific attachment.

8. A method of detecting the presence or absence of an analyte or ligand in a liquid sample comprising:
    a) obtaining a sample fluid;
    b) applying the sample fluid to a chromatographic specific binding assay strip device, said device comprising:
        i) a non-permeable platform strip;
        ii) a permeable membrane testing strip positioned on top of the non-permeable platform strip, said permeable membrane testing strip comprising at least one capture reagent site specific for the analyte being tested;
        iii) a capture reagent positioned at each of said at least one capture reagent site;
        iv) a sample receiving pad positioned on top of and at a proximal end of the non-permeable platform strip while in contact with a proximal end of the permeable membrane testing strip;
        v) a reservoir pad positioned on top of and at a distal end of the non-permeable membrane testing strip while in contact with a distal end of said permeable membrane test strip;
        vi) a semi-permeable membrane positioned on top of said sample pad; and
        vii) a conjugate pad positioned on top of said semi-permeable membrane, said conjugate pad comprising a permeable membrane containing a conjugate;
    c) allowing the liquid sample, added to said conjugate pad, to travel through said semi-pervious membrane, allowing for extended mixing of the sample and the conjugate, thereby forming a conjugate-bound analyte, before traveling along the length of the membrane, wherein said capture reagent at said capture reagent site binds to said conjugate bound analyte, thereby forming a complex; and
    d) detecting said complex and relating it to the presence or absence of the analyte in the sample.

* * * * *